United States Patent [19]
Loridon et al.

[11] Patent Number: 5,550,382
[45] Date of Patent: Aug. 27, 1996

[54] PROCESS AND APPARATUS FOR COMPACTING INFORMATIONS TO BE STORED AND PROCESSING SAID COMPACTED INFORMATIONS

[75] Inventors: Joël Loridon; Jean-Luc Ma, both of Manosque; Alain Marini, Vinon/Verdon; Michel Latu, Montbonnot, all of France

[73] Assignee: Commissariat A L'Energie Atomique, Paris, France

[21] Appl. No.: 426,157

[22] Filed: Apr. 21, 1995

[30]   Foreign Application Priority Data

Apr. 22, 1994 [FR]  France .................................. 94 04871

[51] Int. Cl.$^6$ .......................... G01N 23/222; H03M 7/48
[52] U.S. Cl. ................... 250/390.04; 250/390.01; 341/87
[58] Field of Search ...................... 250/391.04, 391.01; 378/901; 364/413.16; 341/87

[56]  References Cited

U.S. PATENT DOCUMENTS

| | | |
|---|---|---|
| 3,636,353 | 1/1972 | Untermyer . |
| 4,518,947 | 5/1985 | Poston et al. .............................. 341/87 |
| 4,580,056 | 1/1986 | Kaiser et al. . |
| 4,684,923 | 8/1987 | Koga ......................................... 341/87 |
| 4,897,550 | 1/1990 | Bernard et al. . |

FOREIGN PATENT DOCUMENTS 0307271  11/1989  European Pat. Off. .

OTHER PUBLICATIONS

Proceedings of the International Conference on Nuclear Fuel Processing and Waste Management, Aug. 24–28(1987)Paris, France, pp. 1509–1516, Beroud, Y. et al. "Measurement of Alpha Emitters. . . ".
La Technique Moderne 69 (7–8), 41–43(1987) C. Lambermont "Un generateur. . .".

Primary Examiner—Davis L. Willis
Assistant Examiner—Richard Haing
Attorney, Agent, or Firm—Michael N. Meller

[57]  ABSTRACT

The invention relates to a process and an apparatus for compacting binary informations, then reconstructing and processing them in delayed time or with a time lag. It consists of compacting the binary informations by posting during a given cycle informations received on several channels and then associating non-zero information sums with memory channel numbers. It then consists solely of reconstructing the useful informations by coding them in cycle table form. Applied to nuclear fission, this invention consists of delayed time processing of tables in order to determine the proportion of neutrons induced by a fission and neutrons coming from other reactions.

16 Claims, 9 Drawing Sheets

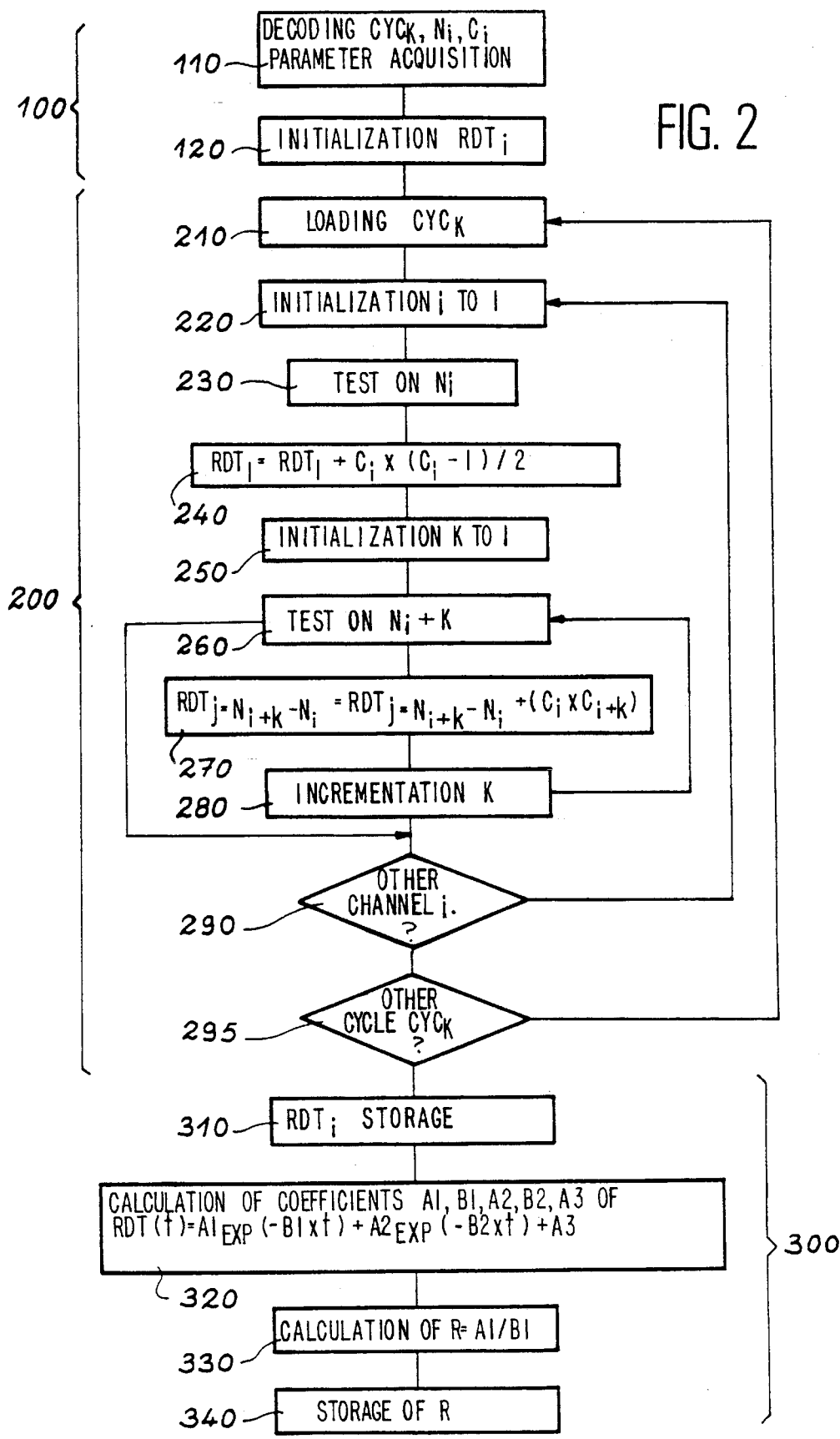

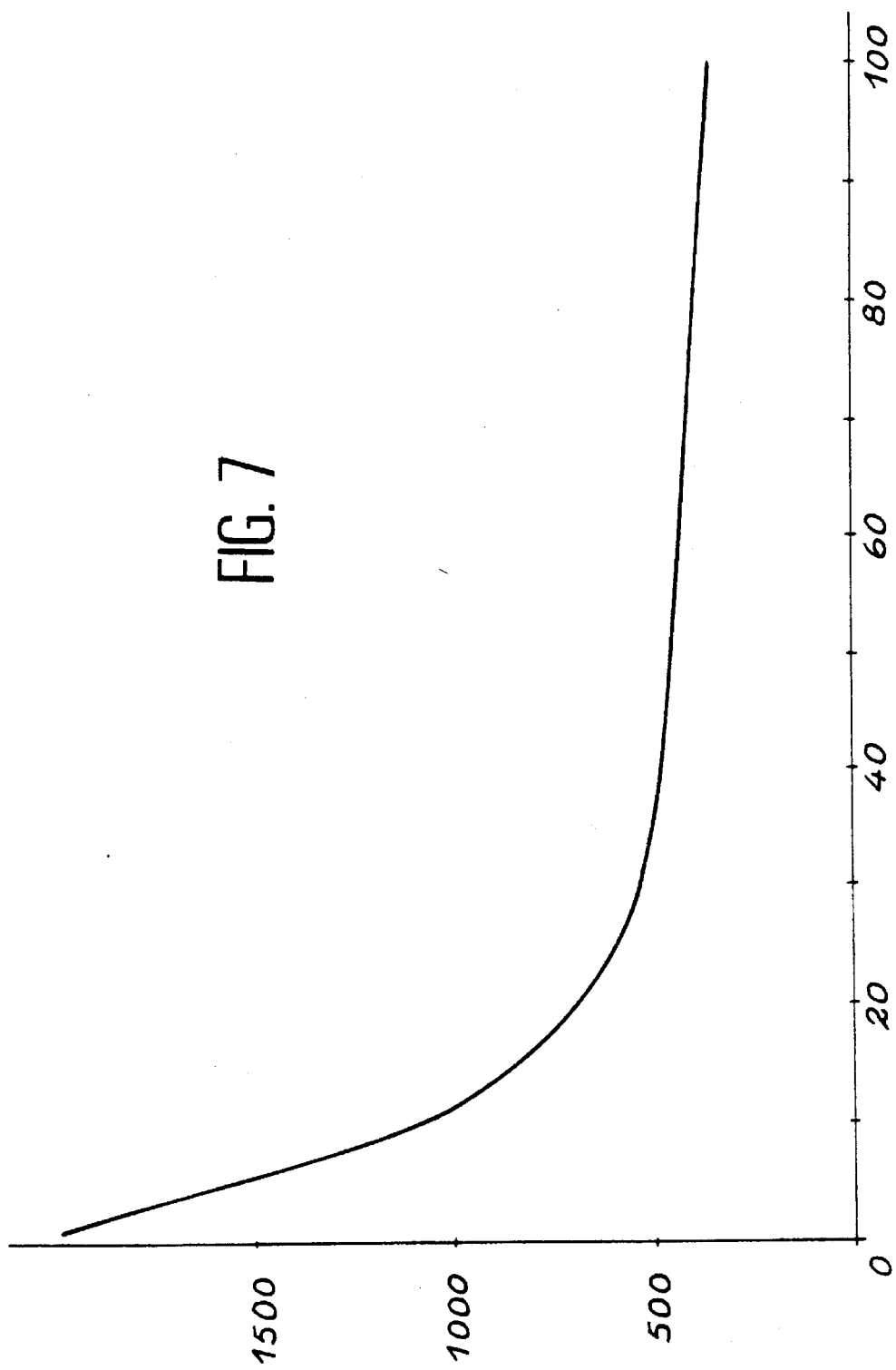

PROCESS AND APPARATUS FOR COMPACTING INFORMATIONS TO BE STORED AND PROCESSING SAID COMPACTED INFORMATIONS

DESCRIPTION

TECHNICAL FIELD

The present invention relates to a process and an apparatus for compacting binary informations, storing them and then reconstructing and processing them. It more particularly relates to a process and an apparatus for compacting and storing a train of electrical pulses from radiation detectors and then reconstructing and processing with a time lag the said pulses in order to determine their possible time correlation.

The invention is used in the field of the characterization of fissile material more particularly contained in radioactive waste. This characterization makes it possible to classify the radioactive waste packages with a view to their storage, particularly by an evaluation of the nature and quantity of the heavy nuclei (fissile material mass) contained in said packages.

PRIOR ART

In the field of the characterization of fissile material, known radioactive methods permit a non-intrusive and non-destructive testing or inspection of waste packages. This fissile material characterization utilizes the detection of neutron and/or photon radiation associated with radioisotopes constituted by uranium elements such as e.g. $^{235}$U, $^{238}$Pu, $^{239}$Pu, $^{240}$Pu, $^{241}$Pu. The mass quantification generally requires the knowledge of the isotopic compositions (relative proportion) and the measurement of the activity of at least one of these different isotopes.

In order to determine the isotopic composition of the uranium and transuranium elements, it is known to use high energy resolution gamma spectrometry of the deactivation gamma rays of said radioisotopes. The activities of these radioisotopes are generally determined by active or passive neutron measurements.

The passive neutron measurements are based on the detection of neutrons from spontaneous fissions and interactions of alpha particles with light elements also producing neutrons. In particular, they make it possible to sign the contributions of the even isotopes of plutonium, such as $^{238}$Pu, $^{240}$Pu or $^{242}$Pu.

In passive neutron measurement, it is of interest to differentiate neutrons from spontaneous fissions from those resulting from the interactions of alpha particles with light elements. Analysis of the coincidences makes it possible to sign the physical origin of the neutrons. This coincidence analysis consists of establishing whether the radiations detected by the detector have been emitted simultaneously or have been emitted at different times. The simultaneously emitted neutrons come from the same spontaneous fission. However, the neutrons emitted at different times do not have the same physical origin, i.e. they do not come from the same fission event.

Thus, coincidence analysis makes it possible to discriminate between neutrons from a spontaneous fission, which in this case are time correlated and so-called "unpaired" or uncorrelated or single neutrons, which are induced by reactions other than spontaneous fission and which result from the interactions of alpha particles with light elements chemically bonded to the radioisotopes (e.g. oxides, nitrides, etc.). This coincidence analysis also permits a characterization of the radioisotopes on the basis of the knowledge of the average number of neutrons emitted during each fission by these radioisotopes (neutron multiplicities).

The active measurements use an interrogation system making it possible to induce nuclear reactions, which are then analyzed in order to quantitatively and sometimes qualitatively determine the fissile material content ($^{235}$U, $^{239}$PU and $^{241}$Pu) of the nuclear waste. Consequently an active detection device comprises a neutron generator or source, a neutron moderator, generally constituted by a hydrocarbon and/or hydrogen material used for lowering the energy level of the neutrons in order to increase the possibility of producing induced fissions and a detector for detecting the neutrons and supplying corresponding signals to a system for measuring and processing these signals. As most neutron detectors are sensitive to thermal neutrons (e.g. detectors proportional to $^{3}$He), the neutrons emitted by spontaneous fission or delayed neutrons or neutrons coming from alpha, n reactions must be slowed down to increase the detection probability.

Coincidence analysis makes it possible to discriminate the correlated neutrons coming from an induced fission and unpaired neutrons either from the neutron source (neutron generator) or parasitic reactions. Coincidence analysis also makes it possible, as in passive neutron measurements, by treating the multiplicities, to differentiate the neutron signatures of e.g. $^{235}$U, $^{239}$Pu, $^{241}$Pu etc. In general, during active neutron measurements, the passive contributions are negligible compared with the induced fissions. Coincidence analysis also makes it possible to reduce the counting part due to unpaired neutrons in the active background noise. When the interrogative sources are of the isotopic type, e.g. Am/Li with a fixed station, the unpaired, interrogator neutron flux is constant with respect to the measurement time. Moreover, under such conditions, the acquisition and processing of the coincidences can be performed by means of devices identical to those used for passive neutron measurements.

Numerous electronic devices are known for performing passive neutron measurements. The JSR12 (registered trademark) device marketed by the Canberra Company is one of the electron devices performing passive neutron measurements. With said JSR12 device can be associated a specific module MSR4 (registered trademark) in order to make it possible to analyze the neutron multiplicities. This MSR4® module analyzes the multiplicities of the neutrons up to order 256 (corresponding to 8 bits in binary coding).

The JSR12® device has shift register means in which the different pulses from the neutron detector are stored, as a function of their arrival order. These shift register means comprise a series of memories, each of which on an instruction from a controller and an electronic clock, records the state of the memory preceding it and the information obtained at the output of said shift register means is consequently "time-shifted". In addition, each neutron pulse taken into account by the JSR12® device causes, after a pre-delay, the accumulation in a "real and accidental" memory of events which have preceded this neutron pulse over a duration equal to or less than the duration of the shift register mean. In addition, each neutron pulse causes after a longer time lag than the pre-delay, the accumulation of uncorrelated events in an "accidental" memory.

In parallel with the aforementioned counting, the specific module MSR4® makes it possible to analyze neutron multiplicities if this is required.

However, the performance characteristics of such a device are limited by the electronic elements constituting it and which as a result of its operating mode, is only suitable for constant pulse rate counting operations.

Thus, such a device cannot be used for pulse-mode, active neutron measurements. The principle of active neutron measurements in the pulse mode consists of bombarding a waste drum optionally containing fissile material traces with a fast neutron burst. Once they have been slowed down, said neutrons have a certain life and can bring about the fission of fissile material traces. Thus, the neutron fluxes have a non-negligible time decay. However, this JSR12®, as well as all the other devices incorporating "shift registers" estimate fortuitous correlations (linked with accidental events), whilst the neutron fluxes have already significantly decreased.

Thus, such devices suffer from the disadvantage of overestimating the number of effective correlations and therefore real events. Thus, with such devices it is necessary to correct the results obtained with respect to the flux decay effects. However, these decay effects come from different stable parameters, such as the design of the measuring cells, the design of the detection blocks, etc., but also and more particularly from the neutron properties of the constituents of the drum of waste material to be characterized.

Thus, it is very difficult with the aforementioned device to carry out pulse mode, active neutron measurements.

DESCRIPTION OF THE INVENTION

The object of the present invention is to obviate the aforementioned disadvantages. To this end it proposes a process and an apparatus making it possible, in passive neutron measurement, to verify the relevance of physical models produced for the analysis of neutron multiplicities, by carrying out the reconstruction of the time distributions between the pulses and to determine a fortuitous correlation rate, whose measurement accuracy is improved compared with the known devices.

In active neutron measurement, the invention permits the differentiation between uncorrelated interrogator neutrons and correlated neutrons from an induced fission. Moreover, in the pulse mode, it makes it possible to take into account fast time evolutions of the different neutron populations present and to directly obtain real coincidence rates.

More specifically, the invention relates to a process for compacting binary informations to be stored, resulting from the recording of signals detected by a neutron detector, and the reconstruction of the thus compacted informations with a view to their processing. This process comprises:

a) recording the detected signals over a total acquisition time corresponding to K measuring cycles, each cycle having N channels, whose acquisition time is regulatable;

b) for each cycle, accumulating on each input channel, the signals detected during a sampling time corresponding to the acquisition time of a channel;

c) for the acquisition time of a channel, forming the binary sum of the individual informations received in this way on all the channels and which constitutes a global data item;

d) allocating to each global data item the number of the corresponding channel;

e) storing each channel number and the global data item associated therewith, when said global data item is not zero in order to constitute a compacted data item;

f) processing in the same way and until coincidence of the N channels occurs, the informations of said cycle;

g) reinitializing all the data in order to perform the recording of the following cycle;

h) when information processing operations have to be carried out, reconstructing the useful informations contained in the compacted data necessary for the processing operations;

i) processing the said useful informations.

Advantageously, the useful information reconstruction stage g) consists of choosing the compacted data to be reconstructed and, for each cycle, writing said compacted data in the form of tables having two columns respectively comprising the channel numbers and the global data items associated with said channels.

According to the process of the invention, the processing stage h) consists, for all the cycles, of constructing a time distribution table (RDT) for chronologically replacing the useful informations in the same histogram in time, said table being constructed from the following data processing instruction:

$$RDT_j = RDT_j + [C_i \times (C_{i+j-1})]$$

in which j is the channel of the histogram in time in which the useful informations are chronologically replaced and i, for each cycle, is the number of the current channel.

This expression, as well as all the other expressions of the same type referred to in the description are data processing instructions in which the equals sign signifies that the term to the left thereof will take on the value the result of the calculation of the terms to the right of the equals sign.

In the particular case where the useful informations are relative to the current channel, use is made of the following data processing instruction:

$$RDT_{j=1} = RDT_{j=1} + C_i \times (C_{i-1})/2$$

When the process of the invention is applied to nuclear fission, the binary informations relate to nuclear fission events. In this case, the processing stage h) consists of determining real events on the basis of the detection of time-correlated neutrons:

by constructing a histogram of the time distribution table (RDT), by determining, using a method of least squares, the coefficients of the expression:

$$RDT(t) = A_1 \exp(-B_1 xt) + A_2 \exp(-B_2 xt) + A_3,$$

in which $A_1$ and $B_1$ are coefficients relative to real events, $A_2$ and $B_2$ are coefficients relative to variable accidental events and $A_3$ is a coefficient relative to time-stable accidental events, by calculating, on the basis of these coefficients, an area $R = A_1/B_1$ corresponding to the real events.

Advantageously, this processing stage h) also consists of a calculation of the coincidences on the basis of a statistical analysis of the real events and the accidental events.

According to the process of the invention, the calculation of the accidental coincidences consists of determining, on the basis of the previously reconstructed, total spectrum, the number of accidental events associated with each channel and entered in the following G channels.

The calculation of the real and accidental events consists of determining, for each cycle and for each channel, the number of real and accidental events entered in the G channels following the channel being processed.

The real coincidences are then obtained for each process channel by subtracting from the real and accidental events the standardized value for a cycle of the number of accidental events associated with said channel and by summating for all the processed channels the thus obtained values.

Finally and advantageously, the determination of the mean number of neutrons emitted during each fission (multiplicity) is performed. This multiplicity calculation with respect to the accidental events firstly consists of determining, for each channel and for all the cycles, the distribution of the accidental events by posting to each channel the number of events stored in the G following channels and by counting, on all the cycles and for said channel, the number of times said number of events has been calculated. Secondly and following the calculation of the distribution of the real and accidental events, for the calculation taking place, the distributions of the corresponding accidental events are summated in a specific register.

According to the process of the invention, the calculation of the multiplicity of real and accidental events is performed for each cycle by calculating the number of events entered in the G following channels and by totalizing, in a specific register, the number of times when said number of events has been found.

Finally, the multiplicities are obtained by subtracting the register of accidental events standardized for one cycle from the register of real and accidental events.

The invention also relates to an apparatus for compacting binary informations to be stored and for the reconstruction of useful compacted informations for delayed processing operations, said apparatus comprising:

a sampling circuit comprising a plurality of input channels able to simultaneously receive binary informations during a succession of cycles and a plurality of output channels able to supply sampled informations;

an information shaping circuit comprising a plurality of input channels connected to the output channels of the sampling circuit and an output, said shaping circuit being able to post, for each cycle, the sampled informations simultaneously received on the input channels and supplying at the output a global data item;

a coding circuit having an input connected to the output of the shaping circuit and an output, said coding circuit being able to allocate to each global data item, if the latter is not zero, a number of a memory channel and supply at the output a compacted data item;

a memory having an input connected to the output of the coding circuit and an output connected to compacted data filing means;

processing means able to reconstruct the useful informations contained in the compacted data and for processing said informations;

a control circuit able to control the information and data exchanges between the sampling circuit, the shaping circuit, the coding circuit, the memory and the processing means.

Advantageously, said apparatus comprises synchronizing means connected to the control circuit permitting the acquisition of data in the pulse mode from a signal supplied by a pulse generator.

When implemented in the field of nuclear fission, said apparatus can also comprise:

an electrical neutron generator able to supply a large number of neutrons to a package to be characterized;

a measuring enclosure able to thermalize the neutrons to be supplied to the package;

neutron radiation detection means able to detect neutron radiation resulting from possible fissions induced in the package and for transforming them into binary informations.

BRIEF DESCRIPTION OF THE DRAWINGS

FIG. 2 shows the functional diagram of the reconstruction processing of the time distributions between the events.

FIG. 7 shows the "RDT" curve for the reconstruction of time distributions obtained for a $^{235}U$ sample measured in the active mode.

DETAILED DESCRIPTION OF EMBODIMENTS

In FIGS. 1A to 1E show the different signals obtained and/or used during the process according to the invention. The signals shown in FIGS. 1A to 1E are represented for pulse-mode, active neutron measurements. In such a case, an electrical neutron generator bombards with fast neutrons the package to be characterized. The neutrons emitted by the generator are called interrogator neutrons or interrogator flux. After slowing down in a moderator, these neutrons give rise to fission reactions in the fissile material. The number of such fission reactions is dependent on the quantity of fissile material contained in the package.

The different neutrons detected can be induced fission neutrons or neutrons emitted by spontaneous fission or unpaired neutrons also known as single neutrons. Thus, the aim is to determine on the one hand the quantity of spontaneous and induced fission neutrons and on the other the quantity of unpaired neutrons. The latter can come from a disturbing reaction (from the interpretation standpoint), i.e. a parasitic reaction other than a fission phenomenon. Unpaired neutrons are also interrogator neutrons emitted by the neutron generator.

In the remainder of the present description, phenomena due to an induced fission or a spontaneous fission are also called "real events R", which correspond to phenomena which it is wished to observe. However, phenomena resulting from disturbing reactions are called "accidental events A". All the phenomena obtained will constitute the "real and accidental events R+A".

More specifically, the aim is to determine if the neutrons intercepted by the neutron detector do or do not come from a fission phenomenon. To know whether the intercepted neutrons come from the same fission, it is established whether the said neutrons are time correlated or uncorrelated. Thus, the time correlated neutrons come from the same event, i.e. the same fission, whereas the uncorrelated neutrons come from various reactions and not from the same fission event.

Figure 1A:
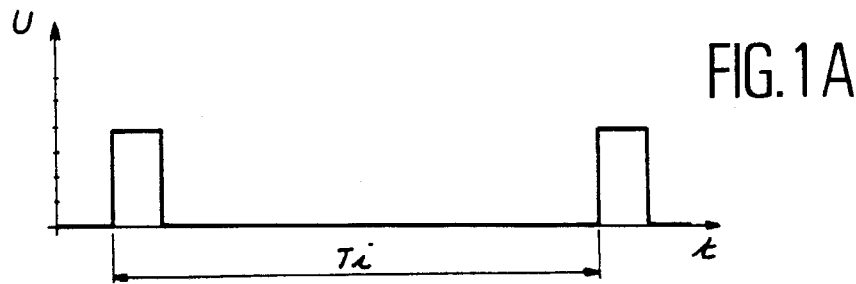
FIGS. 1A, 1B, 1C, 1D and 1E show the different pulses used and obtained during an active neutron measurement in the pulse mode.

FIG. 1A shows the sync signal supplied by the electrical generator and making it possible to determine the duration of a cycle with, on the abscissa the time and on the ordinate the voltage of the sync signal. The time signal $T_i$ represents the duration of a cycle according to the invention.

Figure 1B:
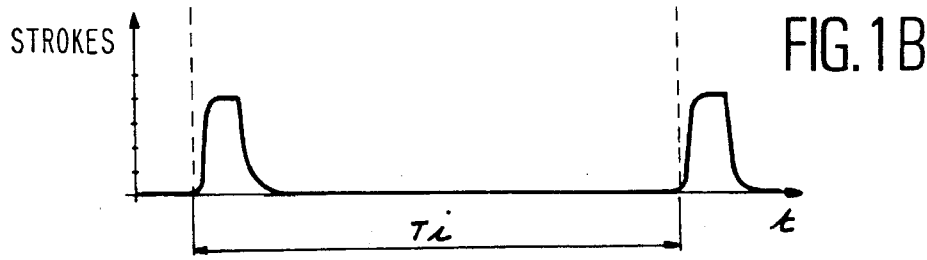

FIG. 1B shows a fast, interrogator neutron flux, i.e. an uncorrelated neutron flux because they are generated by the electrical generator. In FIG. 1B is represented on the abscissa the time and on the ordinate the number of strokes, i.e. the number of fast neutrons received during a sampling time.

Figure 1C:
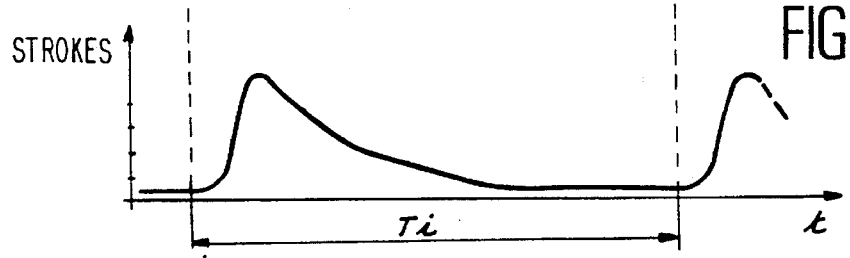

FIG. 1C shows the thermal neutron flux, i.e. of physically uncorrelated neutrons from the electrical generator and slowed down in the measuring cell. In FIG. 1C the time is plotted on the abscissa and the number of strokes on the ordinate.

Figure 1D:
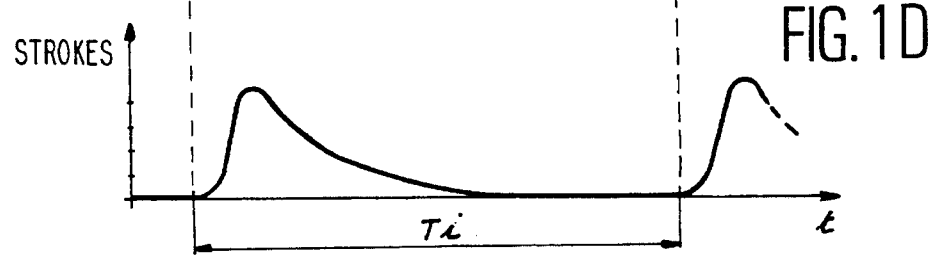

FIG. 1D shows the prompt neutron flux obtained from the induced fissions. In FIG. 1D the time is plotted on the abscissa and the number of strokes on the ordinate.

Thus, in FIGS. 1B to 1D it is possible to see the evolution during a cycle $T_i$ of fluxes of respectively fast, thermal and prompt neutrons resulting from a fission induced by an interrogator neutron flux.

FIGS. 1C or 1D make it possible to see that the flux of neutrons intercepted by the neutron detector have a certain decay at the end of the cycle $T_i$, which is explained by the fact that, in order to be intercepted, the neutrons have been voluntarily slowed down (as explained hereinbefore).

Figure 1E:
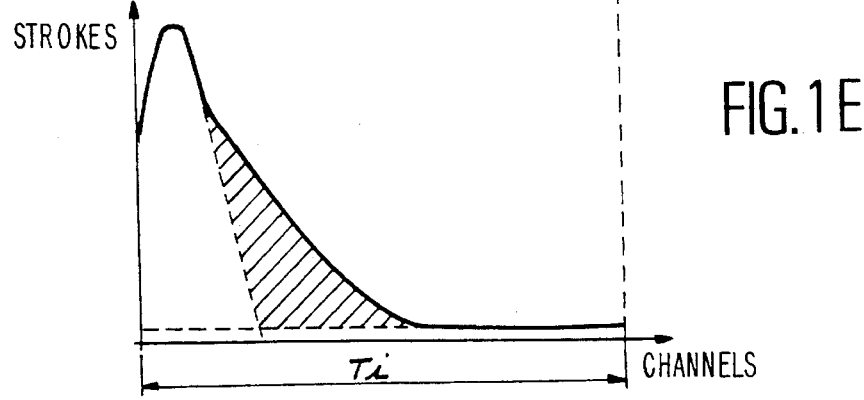

FIG. 1E shows the curve obtained for a total count of the neutrons intercepted by a neutron detector. On the abscissa is plotted the channels of a memory and on the ordinate the number of strokes. The curve represents the total spectrum of neutrons from the neutron generator, the induced fission and possible disturbing reactions. In FIG. 1E, the hatched area represents the useful signal corresponding on the one hand to neutrons emitted during the same induced fission and which constitute the real events and on the other to neutrons of different origins (alpha, N reactions with light elements or interrogator neutrons of the generator) and which constitute the accidental events.

Within the useful signal the invention makes it possible to differentiate the part of the real events R and that of the accidental events A.

The process according to the invention involves several main stages namely a stage of compacting the binary informations to be stored, a stage of reconstructing and analyzing compacted informations and stages of processing decompacted informations.

According to the preferred embodiment of the invention which has been described up to now, these compacted and then decompacted informations relate to nuclear fission events. These binary informations represent, in data processing operations, the electrical pulses supplied by the neutron detector. As explained hereinbefore, when a fissile material element is bombarded by an interrogator neutron burst, said material element produces by fission induced neutrons. A neutron detector then intercepts these induced neutrons and also the interrogator neutrons supplied by the generator and all the other neutrons which can result from said fission or reactions in parallel therewith. This neutron detector is also able to transcribe the neutrons received in the form of electrical pulses. These electrical pulses coded in the form of binary informations have to be compacted in order to store them in a minimum memory space and then the aim is to reconstruct them with a view to processing them with a time lag.

More specifically, the binary information compacting stage, called stage 0 consists:

during a sampling time, receiving on a plurality of input channels, in successive or simultaneous manner, the detected signals, for each of these sampling times, forming a binary sum of the signals received simultaneously on several input channels, as well as successively on each of them;

posting, for the duration of a channel $T_i$, the number of said informations received, this number constituting a global data item $C_i$;

allocating to each of these global data items $C_i$ the number of the corresponding channel $N_i$.

If the global data item $C_i$ is not zero, each group constituted by the channel number $N_i$ and the global data item $C_i$ associated with this channel number is then compacted and filed. In the opposite case, i.e. if the global data item $C_i$ is zero and consequently has no useful information, the global data item $C_i$ is not stored.

As explained hereinbefore, the process according to the invention then consists of reconstructing the compacted informations in order to be able to process them. This compacted information reconstruction stage called stage 1 consists of decompacting the useful informations, which means that all the zero global data items which have not been stored do not have to be reconstructed. Thus, this process leads to a memory space gain of a significant level, as well as a time gain, because it ensures that only useful informations are compacted and decompacted. It also leads to a very useful transmission time gain with respect to pulse-type active measurements, because the time available between the interrogator pulses is very short.

More specifically, the file to be processed (i.e. the file having the compacted data item $C_i$ to be processed) is loaded into the memory. The global data items, filed in binary form, are then converted into the form of a table $CYC_k$. Each table $CYC_k$ describes a cycle of measurements and has in the first column the numbers of the channels $N_i$ and in the second column the global data items $C_i$. The total number k of filed cycles is calculated. When these tables $CYC_k$ have been reconstructed, the global data items $C_i$ can be processed.

This processing of global data items consists, for each cycle table $CYC_k$, in a stage 2 of constructing a time distribution table RDT permitting the replacement of the useful informations of the same cycle in the chronological order of their arrivals on the input channels of the apparatus. In this stage and for each time cycle k (with k varying from 1 to K) a table $RDT_3$ is constructed (with j varying from 1 to I). This table is determined for each current channel I between the analysis start channel DEB and the analysis finish channel FIN, on the basis of the expression:

$$E1: RDT_j = RDT_j + [C_{i+j-1})$$

in which i represents the channel being processed and in which j can vary from 2 to I and represents all the following channels, taking account of the zero content channels.

In the particular case where j=1, the table $RDT_1$ is calculated from the expression:

$$E2 = RDT_1 = RDT_1 + C_i \times (C_{i-1})/2.$$

The RDT processing also consists of a stage 3 relative to the calculation of pseudo-periods and real events. When the analysis of the final cycle table $CYC_k$ is ended, the table $RD_j T$ is filed with a view to a possible display. It is possible to determine by the method of least squares, the coefficients A1, B1, A2, B2 and A3 of the expression:

$$E3: RDT(t) = A1\ exp(-B1xt) + A2(exp-B2xt) + A3$$

in which the coefficients A1 and B1 are relative to the correlated populations, i.e. to correlated neutrons coming from the same fission event. The coefficients A2 and B2 relate to variable uncorrelated neutrons coming from events other than induced fission events. The coefficient A3 relates to time-stable events.

The determination of these coefficients makes it possible to know, on the histogram, the area corresponding to the real coincidences, i.e. to the real events resulting from the induced fission. This area of the real events R is equal to the ratio A1/B1. This area can be expressed either in strokes or in strokes per second. It can also be expressed in a form standardized for a reference generator emission.

More specifically reference can be made to the functional diagram of FIG. 2 to have an overall idea of the RDT processing with:

stage 1 of reconstructing useful informations represented by block 100 in FIG. 2;

stage 2 for the reconstruction of the time distribution table RDT represented by block 200;

stage 3 of the calculation of pseudo-periods and real events represented by block 300.

The useful information reconstruction block comprises a subblock 110 representative of a decoding substage of the $CYC_k$ tables and numbers of channels $N_i$ and their contents $C_i$. This substage also consists of seizing the useful parameters for the processing to be carried out, said parameters e.g. being the cycle time $T_i$, the number of the start channel DEB, the number of the analysis finish channel FIN, the number of the channels to be reconstructed, etc.

The useful information reconstruction block 100 also comprises the subblock 120 representing the initialization stage of the time distribution table $RDT_j$. This initialization consists of zeroing all the lines of the table $RDT_j$, for all the j's from 1 to I, when I is the number of channels to be reconstructed.

The RDT table construction block 200 comprises a subblock 210 for loading the $CYC_k$ cycle table associated with the current cycle k. The subblock 220 represents the initialization substage of the current channel i to 1. In the subblock 230 a test is carried out on the number of the current channel $N_i$. This test consists of verifying if the number of the current channel $N_i$ exceeds the number of the analysis start channel DEB and if it is below the number of the analysis finish channel FIN from which has been subtracted I-1 channels. Thus, this test consists of proving the equations:

$$Ni>DEB \text{ and } Ni<(FIN-I+1).$$

The subblock 240 represents the substage of calculating the line 1 of the RDT table, i.e. the value of RDT for the first channel. This RDT value is determined from the expression:

$$E2: RDT_{j=1}=RDT_{j=1}+C_i\times(C_i-1)/2.$$

In the following subblock 250, the value k of the following channel is initialized to 1. This stage makes it possible to restore from the compacted data Ni and Ci, the unfiled data corresponding to zero global data items Ci. The subblock 260 is a test on the value of the following channel number to be processed and consists of verifying if $$N_{i+K}-N_{\leq I-1},$$

in which I is the total number of channels to be reconstructed. In the case where the test is negative, the following channel being processed k is outside the analysis dynamics and marks the end of the reconstruction of the histogram for the current channel i. The process then passes to the subblock 290.

The subblock 270 represents the substage of determining the RDT value for the channel $N_{i+k}$–Ni. This RDT value is determined from the expression:

$$E1: RDT_{j=Ni+k-Ni}=RDT_{j=Ni+k-Ni}+(C_i\times C_{i+k}).$$

In the subblock 280 incrementation by 1 takes place of the value of the following channel to be processed k. The processing is then taken up again at block 260.

The subblock 290 is a test on the presence of at least one other current channel i for which processing operations have to be carried out. If there are channels i other than those already processed, the processing is taken up at block 220, where i is initialized to 1.

Subblock 295, the final substage of the RDT table construction stage 2, is a test of verifying if other $CYC_k$ cycle tables have to be processed. If at least one other $CYC_k$ cycle table has to be processed, the process resumes at $CYC_k$ loading subblock 210. In the opposite case, it is possible to start stage 3 of calculating the pseudo-periods and real events.

This stage 3, represented by the block 300, involves the substage of storing the $RDT_i$ table (subblock 310). The subblock 320 represents the substage of calculating the coefficients A1, B1, A2, B2 and A3 of the expression:

$$E3: RDT(t)=A1\exp(-B1xt)+A2\exp(-B2xt)+A3.$$

In the subblock 330 the calculation of the area R corresponds to the real events of the fission and is calculated on the basis of the expression:

$$R=A1/B1.$$

Finally, the RDT processing is completed by the substage of storing the previously calculated area R (subblock 340).

Figure 3:
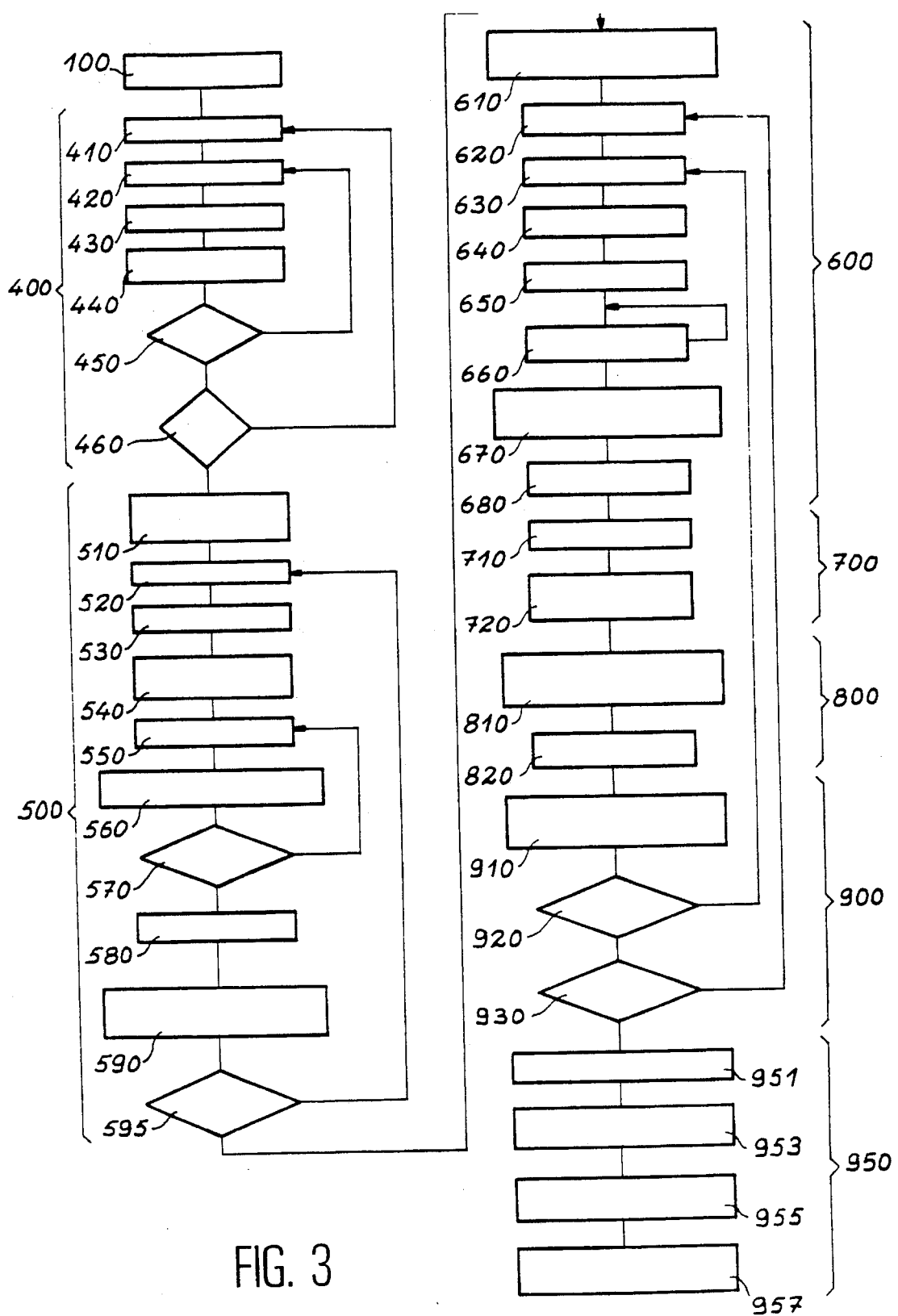
FIG. 3 shows the functional diagram of the statistical processing of the real or accidental time correlations.

FIG. 3 is the functional diagram of the processing permitting the statistical analysis of the coincidences and the determination of the multiplicities, also called R+A processing. This R+A processing consists of determining the real and accidental contributions of the events. In other words it consists of determining the quantity of correlated neutrons with respect to the quantity of uncorrelated neutrons. Thus, for the correlated neutrons reference is made to the real contribution and for the uncorrelated neutrons to the accidental contribution.

FIG. 3 shows all the stages permitting multiplicity analysis. Each of the stages is described in greater detail in FIGS. 4A, 4B and 4C.

Like the RDT processing, said R+A processing has a useful information reconstruction stage 1. Therefore this stage will not be described again here. However, it consists of seizing analysis parameters specific to this process, more particularly the coincidence analysis duration G.

The R+A processing then consists of a total spectrum calculation stage 4. For each channel i, said stage 4 consists of determining for all the k cycles, the total spectrum $SOM_i$ making it possible on the one hand to perform the total count and on the other facilitates the calculations of accidental events A, i.e. the number of uncorrelated neutrons.

Figure 4A:
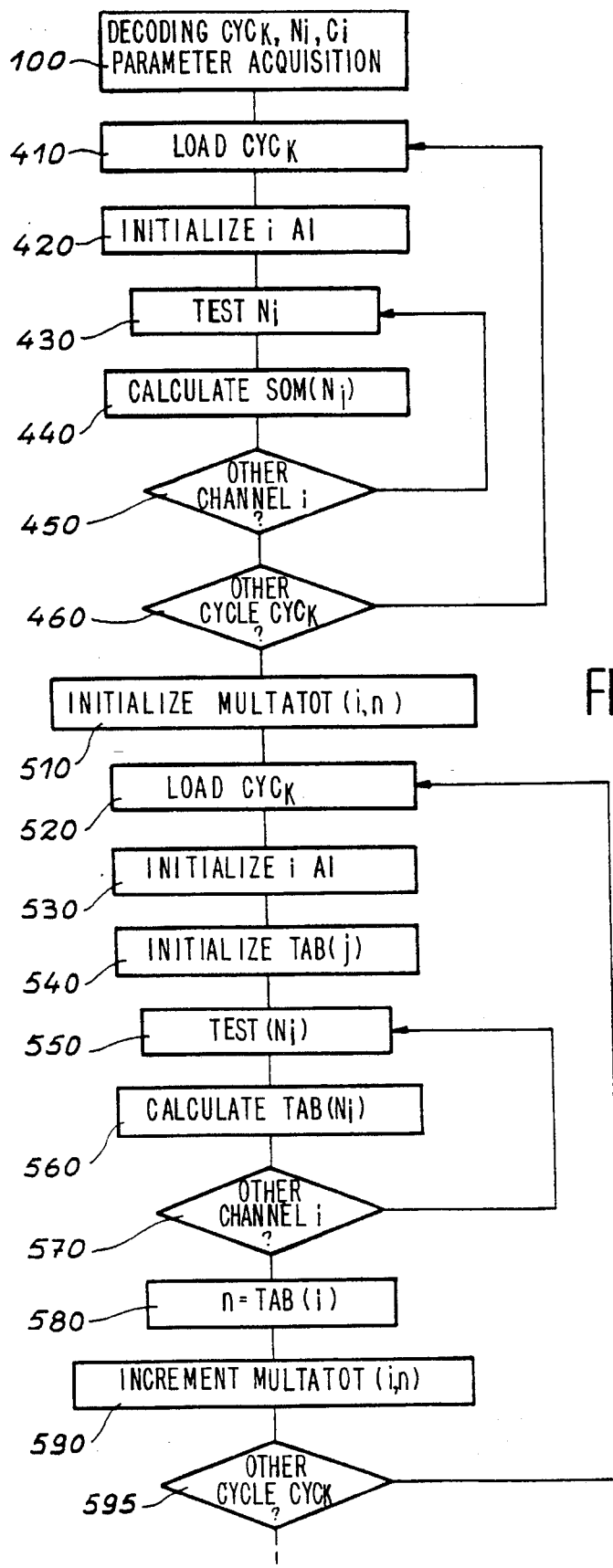
FIG. 4A shows in greater detail the blocks 400 and 500 of the diagram of FIG. 3.
Figure 4B:
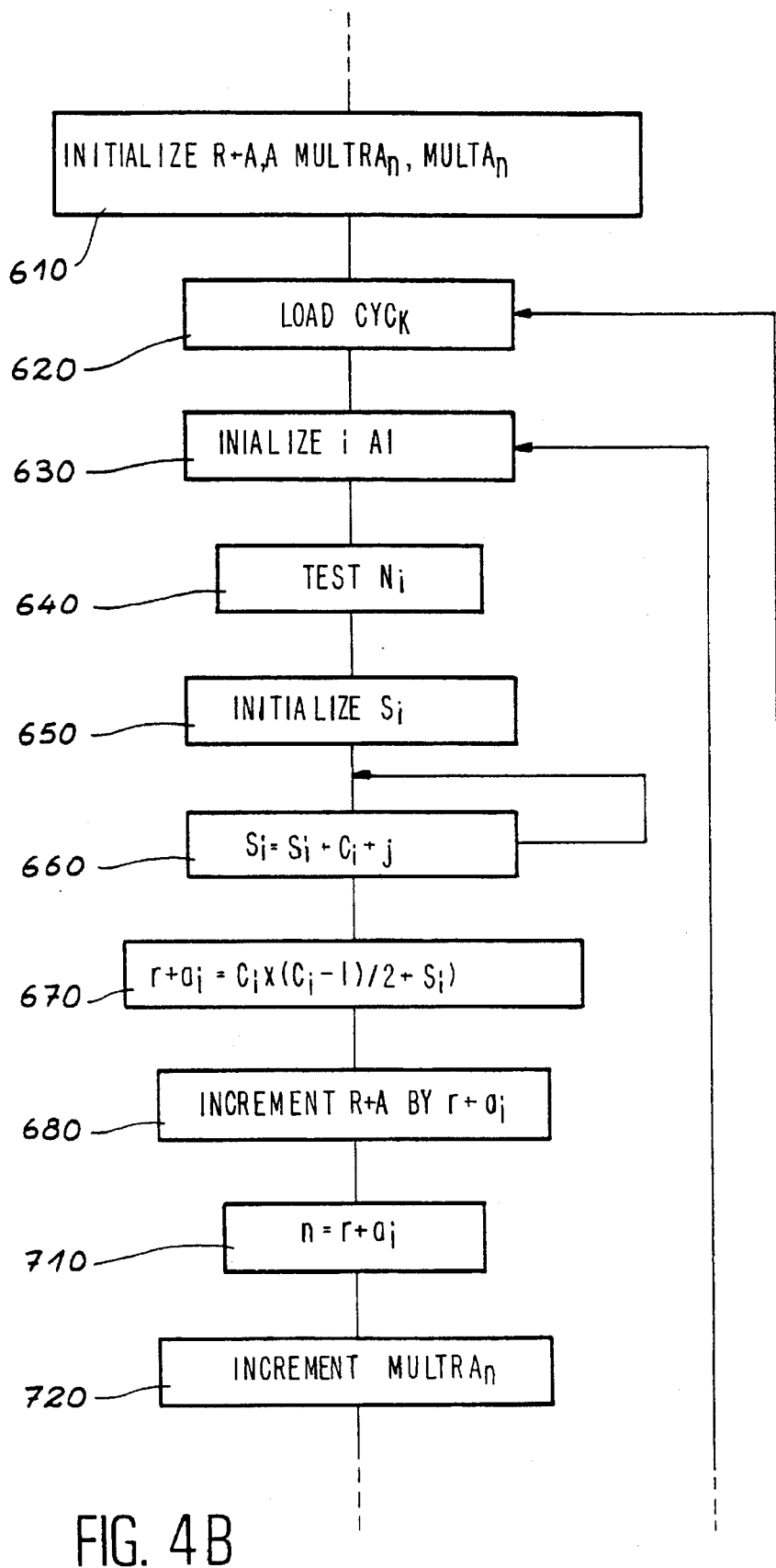
FIG. 4B shows in greater detail the blocks 600 and 700 of the diagram of FIG. 3.

This stage 4 is represented by the block 400 in FIGS. 3 and 4A. The total spectrum calculation stage 4 has six substages, namely:

a substage represented by the subblock 410 and consisting of loading the current $CYC_k$ cycle table;

a substage consisting of initializing the channel i to 1 (subblock 420);

a substage represented by the subblock 430 consisting of a test of the channel number $N_i$, said test seeking to verify if the channel number $N_i$ exceeds the analysis start channel DEB and if said channel number $N_i$ is below the analysis finish channel FIN, so that said substage consists of proving the equations:

$$N_i > DEB \text{ and } N_i < FIN;$$

a substage of calculating the expression $SOM_{(Ni)}$, which is the total spectrum of all the neutrons received by the neutron detector (subblock 440), said spectrum being calculated by means of the expression:

$$SOM_{(Ni)} = SOM_{(Ni)} + Ci$$

the following substage, represented by the subblock 450, consists of a test to establish if at least one other channel i has to be processed and if this is the case the processing resumes at subblock 430, whereas in the opposite case, i.e. if the process channel was the last channel to be processed, one passes to block 460.

In block 460, a check is made to see whether another $CYC_k$ cycle table has to be processed and if this is the case the processing resumes at the $CYC_k$ loading block 410, but in the opposite case the stage 5 of calculating the total multiplicity spectrum is performed.

Stage 5 is represented in FIGS. 3 and 4A by the block 500, which comprises the subblocks 510 to 595. The subblock 510 is an initialization of the file Multatot(i, n) consisting of all the data relative to the multiplicity spectrum in which i represents the channel and n the multiplicity order. This zero initialization is performed for i varying from 1 to I and for n varying from 1 to N:

the subblock 520 represents the substage of loading the current $CYC_k$ cycle table;

the subblock 530 is an initialization of the channel i to 1;

the subblock 540 is an initialization of the variable TAB(j) giving the total number of strokes n recorded in the G channels following the channel i, said zero initialization taking place for j varying from 1 to I;

subblock 550 represents a test on $N_i$ consisting of verifying if the channel number $N_i$ exceeds the analysis start channel DEB plus G, in which is the analysis time, and if $N_i$ is below the analysis finish channel, so that this test proves the equations:

$$N_i > DEB + G \text{ and } N_i < FIN;$$

the subblock 560 consists of calculating the sum of the strokes $TAB(N_j)$ in the G channels following the channel i;

the subblock 570 is a test for verifying if there are other channels i to be processed on the same cycle and if this is the case processing resumes at the subblock 550 of testing $N_i$, whereas in the opposite case processing continues at subblock 580 in which is updated, for said cycle, the file of data relative to the total multiplicity spectrum.

This updating is performed in the subblock 590 by incrementing for each multiplicity found n=TAB(i), the value Multatot(i, n) by one unit:

the subblock 595 is a test for verifying if all the $CYC_k$ cycle tables have been processed and if this is not the case, processing is taken up again at the cycle table loading subblock 520, but if it is the case processing is continued by the R+A calculating stage 6.

The R+A calculating stage 6 consists of evaluating the number of real and accidentical events. This stage 6 is represented by the block 600 in FIGS. 3 and 4B and comprises:

a first substage (subblock 610) consisting of initializing the parameters R+A, A $MULTRA_n$, $MULTA_n$ in which R+A is the number of accidental and real events, A being the number of accidental events, $MULTRA_n$ and $MULTA_n$ being the respective multiplicity files of R+A and A;

the subblock 620 represents the current $CYC_k$ cycle table loading substage;

in the subblock 630, the current table i is initialized to 1;

the subblock 640 is a test on $N_i$ consisting of verifying if the number $N_i$ of the channel i is equal to or greater than the analysis start channel number and strictly below the analysis finish channel number from which is deducted G-1;

the substage represented by the block 650 consists of initializing the counter $S_i$ to zero;

the subblock 660 represents the calculation of the number of pulses inscribed in the analysis time G following the current channel i and calculation in said substage of $S_i$ for j varying from 1 to G-1, in the case where $N_{i+j} - N_i$ if strictly below G, said calculation taking place on the basis of the expression:

$$S_i = S_i + C_{i+j}.$$

The subblocks 670 and 680 represent the substage consisting of determining, for the channel number $N_i$, the total number of real and accidental events on the basis of the following expressions:

$$E4: r + a_i = C_i \times [C_i - 1)/2 + S_i]$$

and $$E5: R + A = R + A + r + a_i.$$

The R+A processing process also involves a stage 7 of decoding the multipolar order of the real and accidental events R+A. This decoding is obtained, for the channel $N_i$, by incrementing the corresponding multiplicity register. This stage 7 represented by block 700 in FIGS. 3 and 4B comprises the subblock 710, where the multiplicity order n is made equal to r+ai. This stage 7 also comprises the substage relative to the subblock 720 and consisting of incrementing the total multiplicity file MULTRA(n) by 1.

Figure 4C:
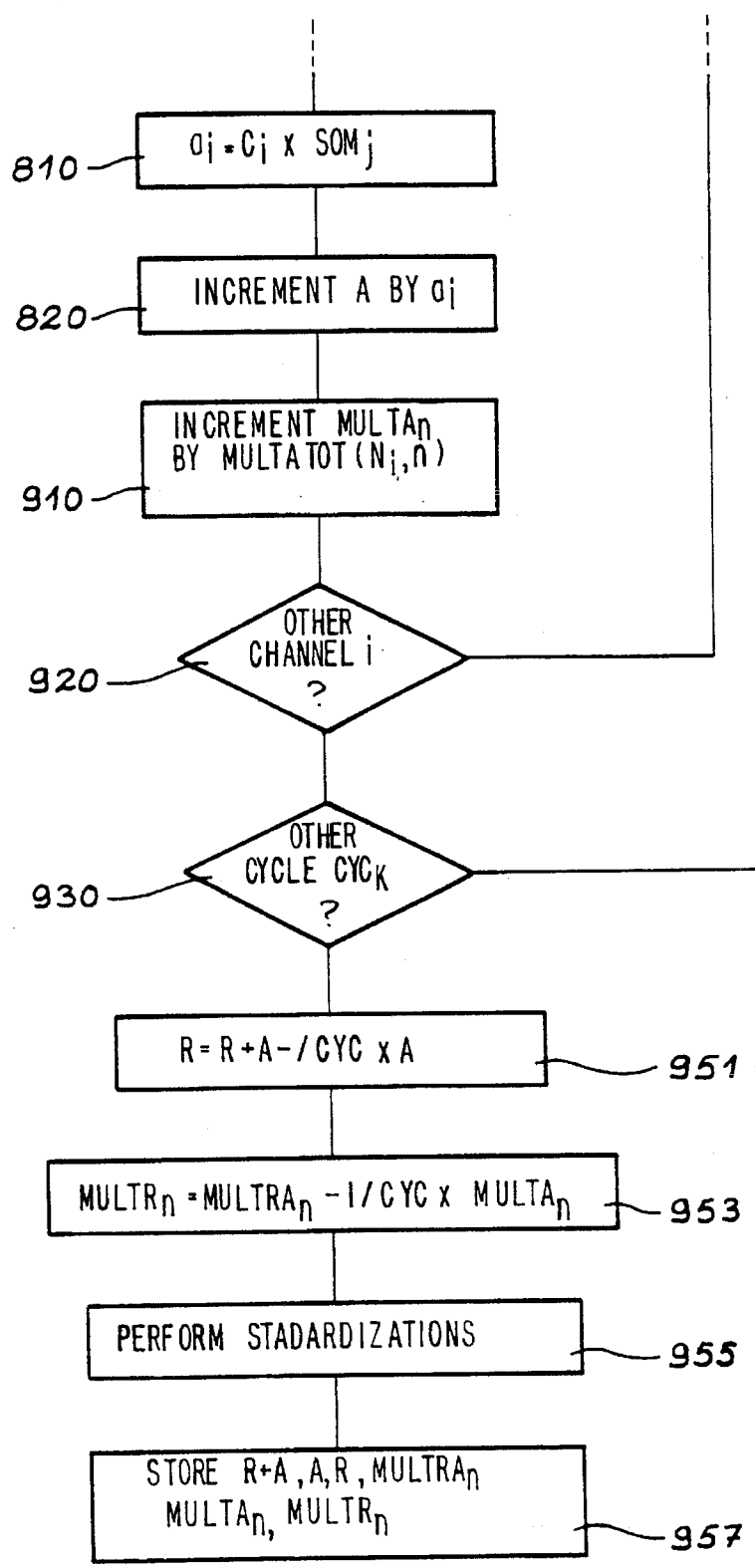
FIG. 4C shows in greater detail the blocks 800, 900 and 950 of the diagram of FIG. 3.

The R+A processing involves an eighth stage, namely stage 8 of calculating accidental events. Stage 8 is represented in FIGS. 3 and 4C by block 800. For the channel $N_i$ and for all the available cycles, a calculation takes place of the sum of the events inscribed on the basis of the channel number $N_i$ and for the analysis time of G channels. This sum is calculated on the basis of the expression:

$$E6: a_i = C_i \times \sum_{N_1}^{N_i+G-1} SOM_j.$$

Thus, this calculation of $a_i$ represents the accidental events for the channel number $N_i$.

The subblock 820 represents the stage consisting of incrementing the total number of accidental events A by the predetermined number $a_i$.

The R+A processing can also comprise a stage 9 of decoding the multiplicities of the accidental events. Thus, for channel number $N_i$ being processed, the accidental multiplicities are calculated from the file $MULTATOT(N_i, n)$. Thus, stage 9 comprises a subblock 9, 10 consisting of incrementing $MULTA_n$ of the $MULTATOT(N_i, n)$ file. The subblock 920 is a test for verifying if all the channels i have been processed. If this is the case processing is taken up again at the initialization subblock 630 for the channel i. If it is the case processing continues at subblock 930.

Subblock 930 is a test for verifying if all the $CYC_k$ cycle tables have been processed. If this is not the case, processing resumes at the $CYC_k$ cycle table loading subblock 620. If it is the case processing continues with stage 10.

The R+A processing can continue with the stage 10 of editing and/or filing the analysis results. Thus, after processing all the $CYC_k$ cycle tables, the calculation of the real events is obtained by subtracting the standardized number of accidental events from the total number of cycles. This stage 10, represented by block 950 in FIGS. 3 and 4C comprises a substage (subblock 951) of determining the number of real events R on the basis of the expression:

$$E7: R = R + A - 1/CYC \times A.$$

For each multiplicity order n, the part of the real events (substage 953) is then calculated by means of the expression:

$$E8: MULTR_n = MULTRA_n - 1/CYC \times MULTA_n.$$

Subblock 955 represents a standardization stage with respect to the emission by the reference generator. Subblock 957 represents the filing and editing of the results obtained, either in strokes, or in strokes per second.

Figure 5:
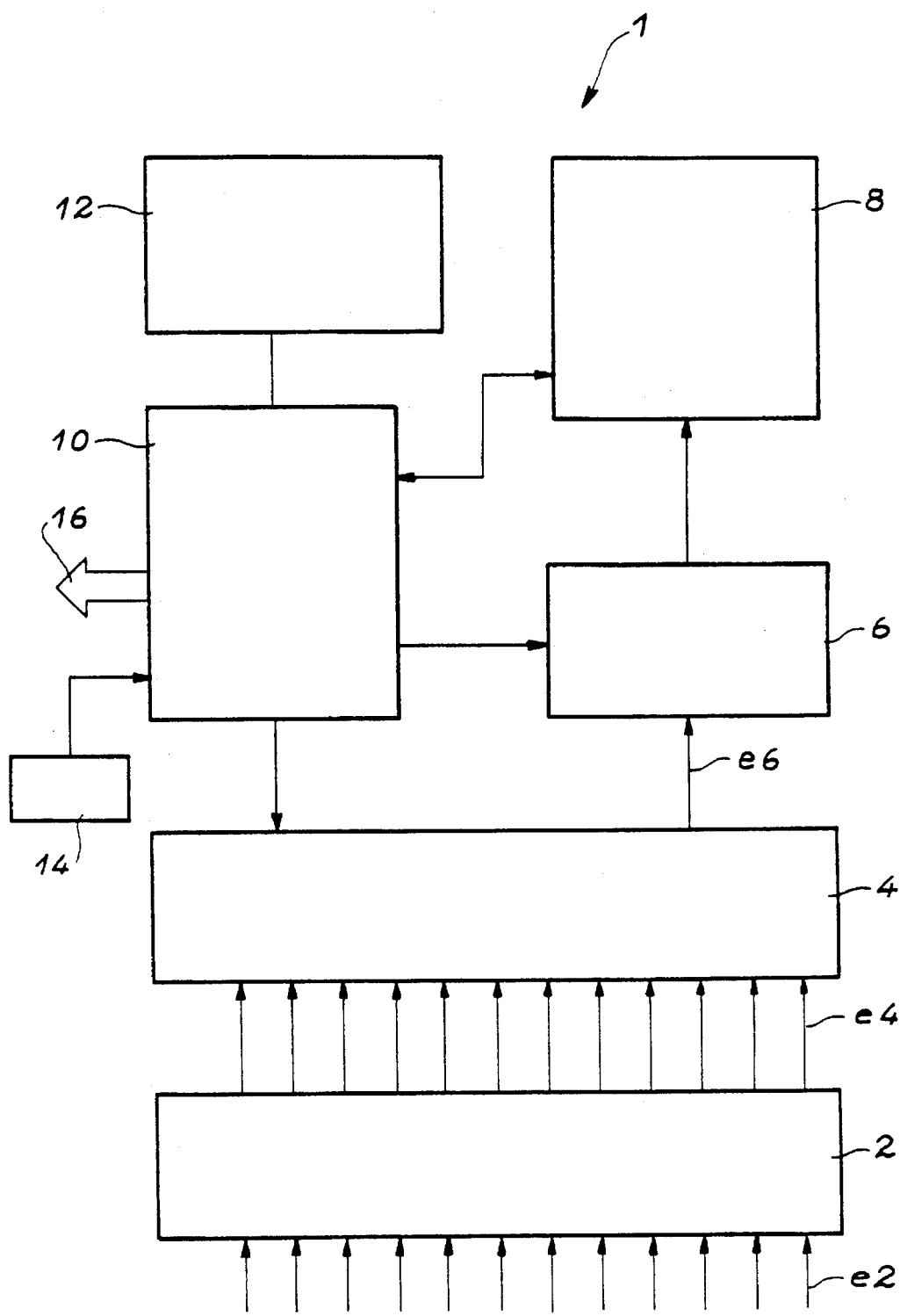
FIG. 5 shows diagrammatically the apparatus according to the invention.

FIG. 5 shows the apparatus 1 for performing the above-described process. This apparatus comprises an input circuit also known as the sampling circuit 2. This sampling circuit 2 has a plurality of input channels e2 (12 channels in the preferred embodiment) enabling said circuit to simultaneously receive several binary informations or electrical pulses. This sampling circuit 2 samples with a frequency F (e.g. approximately 10 MHz), the state of the inputs E2. This sampling is carried out for a given channel duration (1 to 999 μs).

The result of this sampling is transmitted to the shaping circuit 4 by the access channels E4. Thus, the sampling circuit 2 has the advantage of transmitting to the shaping circuit 4 informations with a time resolution between two pulses arriving successively on the same channel of 1/F (for the above example, 1/F is equivalent to 100 ns).

This shaping circuit 4 has electronic means for posting, for each channel, the sampled informations which have been simultaneously received on the input channels E2. The function of this shaping circuit 4 is substantially similar to that of a scaler. This circuit 4 integrates, on the order of the controller 10 (to be described hereinafter) and for an inspection time $T_i$, which corresponds to the duration of a channel, the samplings transmitted thereto of the different input channels E4. Thus, for example, two pulses present simultaneously on different channels are posted (binary sum). At the end of the inspection time $T_i$ (duration of a channel), the shaping circuit 4 transmits to a coder 6 the sum of the thus calculated strokes $C_i$. It is pointed out that a stroke is the number of pulses calculated for each sampling.

The advantage of this shaping circuit 4 is that when it is associated with the sampling circuit 2 it permits a considerable reduction of dead time existing during coincidence analyses. The circuit 4 makes it possible to obtain a counting rate of approximately $10^6$ cps without any counting loss.

The sum of the strokes $C_i$ calculated by the shaping circuit 4 constitutes a global data item. Each global data item is transmitted by the connection E6 to a coding circuit 6. The function of the coding circuit 6 is to generate the number of the current channel $N_i$.

For the preferred embodiment of the apparatus according to the invention with the number of channels 1024, the circuit 6 generates a current channel number from N=1 to N=1024.

For the current channel $N_i$, the coding circuit 6 tests the transmitted value $C_i$. If this value strictly exceeds zero, the circuit 6 transmits to the buffer store 8 a coded word (e.g. of 16 bits) representing the number of the channel $N_i$ and its content $C_i$. This coded word is called "compacted data item" In the case where the global data item $C_i$ is zero, the coding circuit 6 increments the current channel. During the processing of the final channel (the 1024 for the proposed example), after its possible coding, the circuit 6 edits a specific character marking the end of the duration of the cycle.

Such a coding circuit 6 makes it possible to reduce to what is strictly necessary the size of the information to be stored, so that only the useful informations (whose content is not zero) are coded.

The apparatus according to the invention also incorporates a buffer store 8 dimensioned in accordance with the counting rates which it is wished to obtain. This store 8 is controlled by the controller 10 and permits the sequential transmission of stored informations to said controller 10. On the order of the controller 10 either the data from the coding circuit 6 are stored in the buffer store 8, or the data stored in the store 8 are transmitted to an e.g. PC-type microcomputer, via the interface buffer 16 in accordance with the FIFO (First in First Out) transmission principle.

The function of the controller 10 is to dialogue with the microcomputer (not shown in the drawings). It also controls the measuring parameters used in the aforementioned process and also controls the different circuits constituting the apparatus 1 according to the invention.

During parametrizing phases, the controller 10 reads the different settings such as the duration of the synchronization delay, the duration per channel $T_i$, the exchange speed, the total number of CYC measuring cycles, etc. and transmits them to the different corresponding circuits whilst initializing them.

During the measuring phases, the controller 10 awaits the appearance of the sync signal and decrements the number of measuring cycles CYC, whilst validating the operation of the shaping circuit, the coding circuit and the buffer store.

It is obvious that the function of the controller has been described in the case where synchronization comes from a synchronization circuit 14 outside the controller 10. However, in certain cases, the synchronization can be supplied internally, i.e. without a synchronizing circuit 14 and is in fact provided by the actual controller 10.

During the measuring cycles, the controller 10 generates the transmission of data between the buffer store 8 and the computer via the interface bus 16. At the end of the current cycle, if there are still cycles to be analyzed, the controller 10 reinitializes all the circuits of the apparatus 1. However, when the current cycle is terminated and it was in fact the last cycle, the controller 10 hands over to the computer and is put into the watch mode.

The apparatus according to the invention also has a synchronizing circuit 14, which is short-circuited when an internal mode synchronization is chosen. This synchronizing circuit 14 transmits to the controller 10 the signal permitting the validation of the acquisition of measuring cycles and their counting.

The apparatus according to the invention also comprises a low voltage/mains power supply 12, which converts the mains voltage into a d.c. voltage for supplying the other circuits of the apparatus.

As has been stated several times hereinbefore, the apparatus has a computer, which is not shown in FIG. 5 in order not to overburden the latter. This computer, which can be of the PC type, permits the filing of the files used during the measurements. During the parametrizing phase, said computer enables the user to obtain measurement parameters which are then to be transmitted to the controller 10. In the measuring phase, said computer dialogues with the controller 10 in order to exchange data and file them in storage means such as a hard disk.

Figure 6:
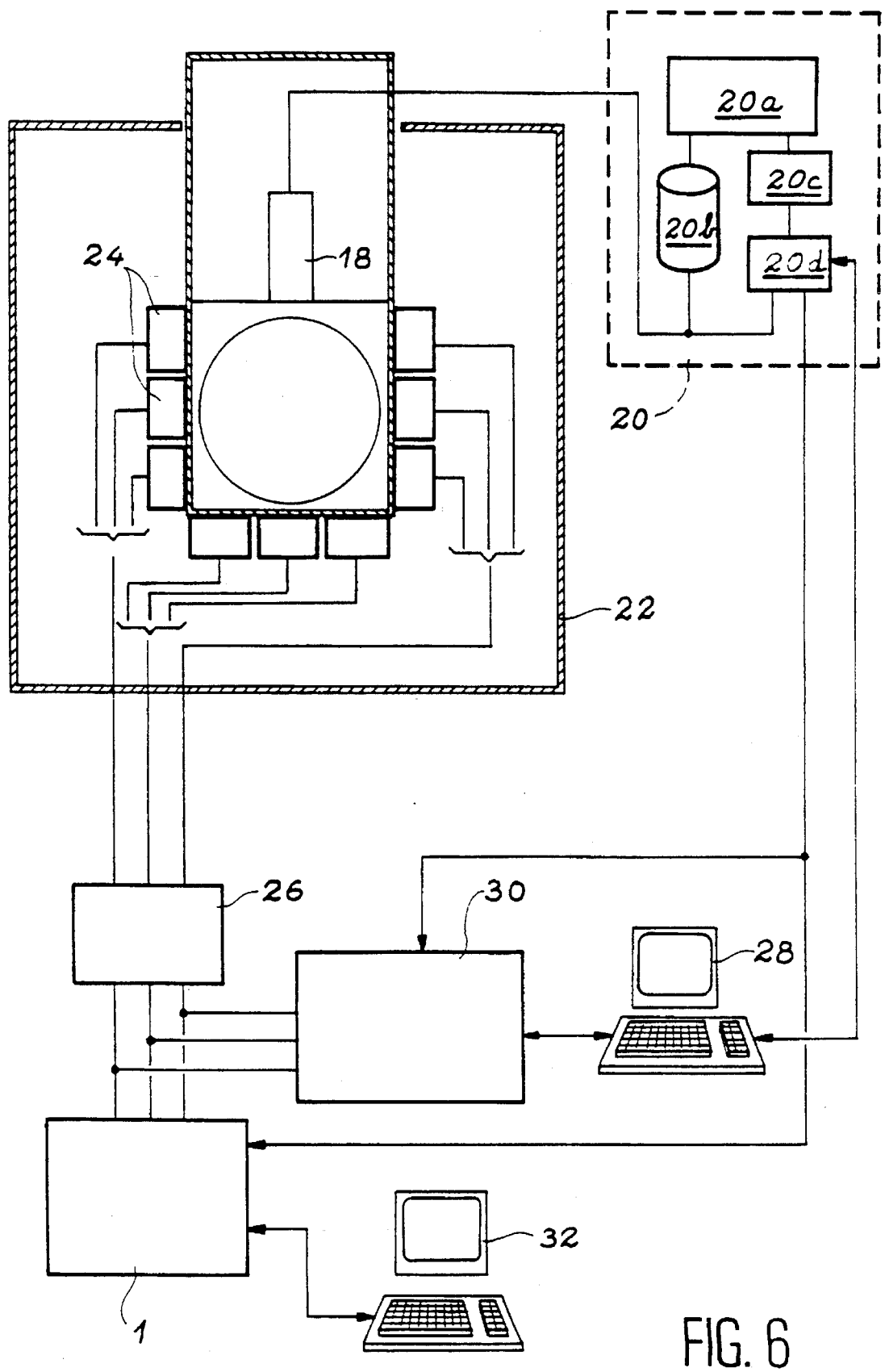
FIG. 6 shows diagrammatically the apparatus according to the invention applied to nuclear fission.

FIG. 6 shows a device for characterizing the fissile material contained in a waste drum. This characterizing device uses the apparatus according to the invention described relative to FIG. 5. This fissile material characterization device also comprises:

an electrical neutron generator 18 emitting neutron bursts for bombarding the interior of the drum to be inspected;

means 20 for the electric supply and control of the generator 18 incorporating a power supply 20a, a low voltage supply 20c, a control circuit 20d and a synchronizing device 20b;

a measuring enclosure 22 incorporating moderator means (such as polyethylene) and reflector means (such as graphite) for thermalizing the interrogator neutrons bombarded by the generator 18;

a plurality of neutron detectors 24 able to detect the neutron radiation induced by the nuclear fission;

an electronic circuit 26 for the power supply of the counters and for the shaping (TTL standard) of the pulses from the detectors 24;

a control/command computer 28 dedicated to the total counting;

scalers 30 receiving at the input on the one hand the sync signal from the synchronizing device 20d and on the other the different TTL signals coming from the power supply and shaping circuit 26;

the apparatus according to the invention 1;

and a filing and processing computer 32 dedicated to the coincidence measurements, the function of said computer 32 having been described in connection with FIG. 5.

The apparatus diagrammatically shown in FIG. 6 utilizes the active neutron interrogation principle. According to this principle, a fast neutron burst is emitted at time t by the neutron generator 18. As a result of matter/neutron interaction processes, these neutrons are thermalized. The fissile material possibly contained in the drum is then exposed to the thermal neutrons which bring about its fission. The detection of the fast neutrons resulting from said induced fission is used for quantifying the fissile material mass contained in the drum.

The apparatus according to the invention shown in FIG. 5 makes it possible to discriminate the events due to the interrogator neutrons from the events due to the induced fission neutrons. Thus, it makes it possible to reduce undesired noise and consequently improve the detection limits of the apparatus proposed in FIG. 6. Moreover, the apparatus according to the invention offers the possibility of performing multiplicity analyses, which makes it possible to characterize the nature (U or Pu) of the fissile isotopes, as well as evaluate a possible contamination by other isotopes such as curium isotopes.

FIG. 7 shows a RDT construction example obtained in active pulse measurement for a sample of approximately 10 g of uranium 235. The conditions under which this curve were obtained are as follows. The neutron generator emitted, at a fixed frequency of 125 Hz, fast neutron bursts at 15 µs intervals. It supplied TTL-type sync signals used for the synchronization of the scalers and the apparatus 1 according to the invention.

The recording obtained corresponds to the following setting: total number of cycles 112500, a channel time of 3 µs per channel and a synchronization time lag of 40 µs. The curve obtained is in the form of the sum of two exponentials, namely a first exponential curve whose pseudo-period is $T_{1/2}$ of approximately 17 µs and a second exponential curve, which decays more slowly in accordance with the life of the interrogator neutrons in the measuring cell.

We claim:

1. Process for compacting binary informations resulting from the recording of signals from a neutron detector and having to be stored and for the reconstruction of the thus compacted useful informations in order to process them, characterized in that it consists of:

a) performing the recording of the detected signals for a total acquisition time corresponding to a number (K) of measuring cycles, each cycle consisting of a number (N) of channels having a regulatable acquisition time, b) for each cycle, accumulating the detected signals for a sampling time corresponding to the acquisition time of a channel, each of these signals representing an individual information, c) for the acquisition time of one channel, forming a binary sum of these individual informations, the thus summated informations constituting a global data item, d) allocating to each global data item the number of the corresponding channel (Ni), e) storing each channel number, as well as the global data item associated therewith, when said global data item is not zero for forming a compacted data item, f) reinitializing each of the data items for performing the recording of the following cycle, g) for performing information processing operations, reconstructing (stage 0) the useful informations contained in the corresponding compacted data items, h) processing said useful informations (stages 1 to 10).

2. Process according to claim 1, characterized in that the useful information reconstruction stage f) consists of choosing the compacted data to be reconstructed and, for each cycle, writing said compacted data in the form of table CYC having two columns respectively incorporating the numbers of the channels ($N_i$) and the global data items ($C_i$) associated with said channels, each table representing a cycle.

3. Process according to claim 2, characterized in that the processing stage h) consists, for all the cycles, of constructing a time distribution table (RDT) for chronologically replacing for each cycle the useful informations in the same histogram in time, said table being constructed from the data processing instruction:

$$RDT_j = RDT + [C_i \times C_{(i+j-1)}]$$

in which i is the channel being processed and j represents all the following channels i taking account of the channels whose content is zero.

4. Process according to claim 3, characterized in that the useful informations relative to the first cycle are determined by the expression:

$$RDT_1 = RDT_1 + C_i \times (C_{i-1})/2.$$

5. Process according to claim 1, in which the binary informations are relative to real or accidental nuclear fission events coming from a projection of neutrons onto a fissile material, characterized in that the processing stage (8) consists of determining the real events from a time-correlated neutron detection:

by constructing a histogram of the time distribution table (RDT), by determining by means of a method of least squares, the coefficients of the expression:

$$RDT(t)=A_1\exp(-B_1xt)+A_2\exp(-B_2xt)+A_3,$$

in which $A_1$ and $B_1$ are coefficients relative to real events, $A_2$ and $B_2$ are coefficients relative to variable, accidental events and $A_3$ is a coefficient relative to time-stable, accidental events, by calculating, on the basis of these coefficients, an area $R=A_1/B_1$ corresponding to the real events.

6. Process according to claim 1, in which the binary informations are relative to nuclear fission events which can be real or accidental, characterized in that the processing stage A consists of a calculation of the coincidences on the basis of a statistical analysis of the real events and the accidental events.

7. Process according to claim 6, characterized in that the calculation of the accidental coincidences consists of determining, on the basis of the total spectrum, the total number of accidental events associated with each channel.

8. Process according to claim 6, characterized in that the calculation of the real and accidental events consists of determining, for all the cycles, the total number of real and accidental events for each cycle.

9. Process according to claim 7, characterized in that the real coincidences are obtained by subtracting the total number of accidental events from the total number of real and accidental events.

10. Process according to claim 6, characterized in that it consists of determining a mean number of neutrons emitted during each fission, said number being determined for all the measuring cycles and for each channel.

11. Process according to claim 6, characterized in that it consists of a calculation of the multiplicity orders of the accidental events by determining for each channel and for all the cycles a multiplicity spectrum of the accidental events by posting the number of stored events in channels G following the channel being processed and totalizing for all the cycles, the number of times where said number of events has been calculated.

12. Process according to claim 6, characterized in that it consists of a calculation of multiplicity orders of real events by the determination, for each channel, of the number of events stored in channels G following the channels being processed and by totalizing, for all the cycles, the number of times where said number of events has been found.

13. Process according to claim 8, characterized in that the real coincidences are obtained by subtracting the total number of accidental events from the total number of real and accidental events.

14. Apparatus for compacting binary informations to be stored and for the reconstruction of useful compacted informations for delayed processing operations, said apparatus comprising:

a sampling circuit (2) comprising a plurality of input channels (E2) able to simultaneously receive binary informations during a succession of cycles and a plurality of output channels able to supply sampled informations;

an information shaping circuit (4) comprising a plurality of input channels (E4) connected to the output channels of the sampling circuit and an output, said shaping circuit being able to post, for each cycle, the sampled informations simultaneously received on the input channels and supplying at the output a global data item;

a coding circuit (6) having an input (E6) connected to the output of the shaping circuit and an output, said coding circuit being able to allocate to each global data item ($C_1$), if the latter is not zero, a number of a memory channel ($N_i$) and supply at the output a compacted data item;

a memory (8) having an input connected to the output of the coding circuit and an output connected to compacted data filing means;

processing means (32) able to reconstruct the useful informations contained in the compacted data and for processing said informations;

a control circuit (10) able to control the information and data exchanges between the sampling circuit, the shaping circuit, the coding circuit, the memory and the processing means.

15. Apparatus according to claim 14, characterized in that it has synchronizing means (14) connected to the control circuit permitting the acquisition of data in the pulse mode from a signal supplied by a pulse generator.

16. Apparatus according to claim 14 in which the binary informations relate to fission events, characterized in that it also comprises:

an electrical neutron generator (18) able to supply a large number of neutrons to a package to be characterized, a measurement enclosure (22) able to thermalize the neutrons to be supplied to the package, means (24, 26) for detecting neutron radiation able to detect the neutron radiation resulting from possible fissions induced in the package and for transforming them into binary informations.

* * * * *